United States Patent [19]

Schwarzchild et al.

[11] Patent Number: 4,834,102

[45] Date of Patent: May 30, 1989

[54] ENDOSCOPE FOR TRANSESOPHAGEAL ECHOCARDIOGRAPHY

[76] Inventors: Jack Schwarzchild, 41 Revonah Ave., Stamford, Conn. 06905; Russel L. Uphoff, Limekiln Rd., West Redding, Conn. 06896; Christopher G. Miller, 7 Grey Squirrel Dr., Norwalk, Conn. 06850

[21] Appl. No.: 160,359

[22] Filed: Feb. 25, 1988

[51] Int. Cl.[4] .............................................. A61B 10/00
[52] U.S. Cl. ......................... 128/662.06; 128/660.09; 73/623
[58] Field of Search ................................. 128/660–663; 73/623, 633

[56] References Cited

U.S. PATENT DOCUMENTS

| | | | |
|---|---|---|---|
| 4,494,549 | 1/1985 | Namba et al. | 128/660 |
| 4,517,985 | 5/1985 | Teslawski et al. | 128/660 |
| 4,587,971 | 5/1986 | Stolfi et al. | 128/660 |
| 4,664,121 | 5/1987 | Sanghvi et al. | 128/660 |
| 4,671,292 | 6/1987 | Matzuk | 128/660 |
| 4,732,156 | 3/1988 | Nakamura | 128/660 |

*Primary Examiner*—Francis Jaworski
*Attorney, Agent, or Firm*—Schweitzer & Cornman

[57] ABSTRACT

An endoscope, especially for transesophageal echocardiography. An encapsulated ultrasonic transducer capsule is provided having a self-contained electromechanical sector scanner. A sealed housing is formed which includes axially aligned tubular sections, one of magnetic material and the other of acoustically transparent plastic. A tubular shaft is journalled axially within the housing for limited sector scanning rotation. A magnetic rotor is fixed to the shaft for operation within the magnetic housing section and a transducer element is fixed to the shaft within the other tubular section. Conductor wires for activating the transducer are fixed at one end of the capsule and extend axially through the tubular shaft for connection to the transducer. Position sensing means are incorporated within the capsule. The construction enables the capsule to be highly miniaturized and greatly improved relative to known devices of this type.

23 Claims, 4 Drawing Sheets

ENDOSCOPE FOR TRANSESOPHAGEAL ECHOCARDIOGRAPHY

BACKGROUND AND SUMMARY OF THE INVENTION

The invention relates to a new and improved endoscope for internal examination and diagnosis using an ultrasonic sector scanner, especially for transesophageal cardiography. More particularly, the invention is directed to a unique construction of a mechanical sector scanner capsule for mounting at the distal end of an endoscope to enable ultrasonic examination and diagnosis to be performed internally. While the invention is particularly adapted for transesophageal echocardiography, that application should be regarded as advantageous and exemplary only, and not as a limitation of the scope of the invention.

In echocardiography, and other diagnostic practices utilizing ultrasound, it is common to utilize an ultrasound transducer device applied externally to the body for the transmission and reception and acoustic pulses. In the so-called B-mode diagnostic procedures, a designated area of the body is scanned with acoustic pulses, and the echoes from such pulses are displayed in real time on a CRT (cathode ray tube 2) display. These procedures are non-invasive and easily performed, and have become used rather widely in a variety of fields, including cardiology.

One of the limitations of echocardiographic diagnosis, using an external transducer element, is the character of the intervening materials between the transducer and the heart (or other organ) being examined. For example, an externally applied acoustic pulse may be attenuated or distorted by the intervening presence of rib material, air pockets from the lungs, etc. This limits the areas from which the heart, for example, may be effectively acoustically scanned from the exterior of the body. In addition, patients having pulmonary disease or obesity problems may not be capable of useful cardiographic diagnosis by externally applied ultrasound.

Heretofore, it has been proposed to mount ultrasonic scanning devices at the distal end of an endoscope device, which can be inserted into the body. For example, for echocardiography, it has been proposed to insert such an endoscope into the esophagus. By this means, it is possible to locate an ultrasonic scanning device at the level of the heart, within the esophagus, and transmit acoustic pulses laterally into the heart. Because of the close positioning of the scanning device, and the minimum amount of intervening material to be traversed, a sharp, high quality echo image can be obtained. Additionally, using an endoscope with a controllably bendable distal end, it is possible to position the scanning device within the stomach, oriented to direct acoustic pulses upward into the heart from below. This provides a viewing perspective which is not possible to achieve using external transducer devices.

Although the use of a transesophageal endoscope for echocardiography has many obvious advantages over external devices, the actual utilization of such devices has been severely limited by the extremely high cost and/or impracticability of the devices heretofore provided. In general, ultrasonic sector scanners are of two types: Electronically driven arrays and mechanical sector scanners. Array devices are well suited for mounting on an endoscope, because they can be highly miniaturized and have no moving parts. The scanning of an arcuate sector is achieved by sequential or phased activation of individual transducer elements physically arranged to project at different angles over the included sector. With a mechanical sector scanner device, a single transducer element is mounted for controlled, high speed rocking motion, being pulsed repeatedly during each scanning cycle.

While theoretically ideal for endoscope application, the use of array scanners for echocardiography and other end uses has been sharply limited by the prohibitively high cost of such equipment. Mechanical sector scanners, on the other hand, while capable of being produced at only a fraction of the cost of that of an array scanner, have up to now been completely unsuitable for practical clinical use and have been employed, if at all, only under laboratory conditions.

Because space requirements are extremely constrained for an endoscope-mounted transducer suitable for passage through the esophagus, for example, the conventional approach to the utilization of mechanical sector scanners in such applications has involved the use of a drive motor mounted at the proximal (external) end of the endoscope and arranged to manipulate an echo device at the distal end through remote drive means. In some cases, an elongated, rotatable drive shaft has been employed; in others, a string and pulley drive arrangement has been used to transmit motion from the remote drive motor to the internal echo device. In practice, these devices have been of very limited usefulness, because of the inherent error in relating, with the necessary precision, the position of the remote drive motor to the position of the internal echo device. The substantial distance between these two devices allows too much stretch and distortion in the intervening drive means.

One attempt to avoid the problems of the remote drive device is represented by the Suwaki et al. U.S. Pat. No. 4,375,818. There, among a variety of proposals offered, is an arrangement in which a drive motor, gear box and rockable mechanical sector scanner are mounted at the distal end of an endoscope, within an oil-filled bag. Such a device is necessarily large and bulky, and not suitable for general clinical use in transesophageal and similar applications. The size of the device is of obvious importance in that, first, it must easily enter and move through the esophageal passage and, secondly, possible discomfort of the patient must be minimized.

A feature of the present invention is the design and construction of a highly reliable, highly precise mechanical sector scanner device, for endoscope mounting, which is entirely self-contained within an extremely small capsule and thus ideally suited for such applications as transesophageal echocardiography. The device of the invention, produceable at a fraction of the cost of electronic arrays, and altogether free of the important disadvantages of prior mechanical scanner devices, is well suited for general diagnostic use.

Pursuant to the invention, a precision mechanical sector scanner device may be contained in a capsule of approximately one cm in diameter and about three cm in length, ideally suited for attachment to the distal end of an endoscope device.

In accordance with one aspect of the invention, a unique form of mechanical sector scanner device is provided, in which a magnetic rotary element and transducer element are fixed to a common shaft, mounted within an oil-filled, sealed, cylindrical capsule for rotation through a predetermined sector scanning angle. The capsule housing comprises two coaxially aligned tubular housing sections joined end to end. One of the housing sections is formed of magnetic material and surrounds the magnetic rotor, while the other housing section is formed of acoustically transparent plastic material and surrounds the transducer element.

To particular advantage, the common shaft, to which the rotor and transducer means are fixed, is of tubular construction, and flexible conductor wires, for activating the transducer, extend through the center of the shaft. These conductors are connected at their outer ends to the transducer crystal, and at their inner ends to a fixed terminal plate. During sector scanning operations, the motion of these conductor wires is limited to a slight back and forth twisting motion.

Position sensing means is contained within the sealed capsule and provides constant feedback of the exact angular orientation of the transducer crystal. This enables the CRT display to be precisely synchronized with the position of the transducer. Moreover, it enables high precision control over the motions of the crystal during its scanning operations.

As a specific advantageous feature, one end of the transducer capsule is formed by a terminal plate having axially projecting conductor pins electrically connected to the various elements within the capsule. This enables the capsule to be literally "plugged in" to a socket board provided at the distal end of the endoscope device. The device of the invention utilizes a practical minimum number of individual parts and derives an optimum level of performance therefrom. This enables the device to be miniaturized without creating excessive cost in the manufacturing operation or compromising performance.

For a better understanding of the above and other features and advantages of the invention, reference should be made to the following detailed description of preferred embodiments of the invention and to the accompanying drawings.

DESCRIPTION OF PREFERRED EMBODIMENTS

Figure 1:
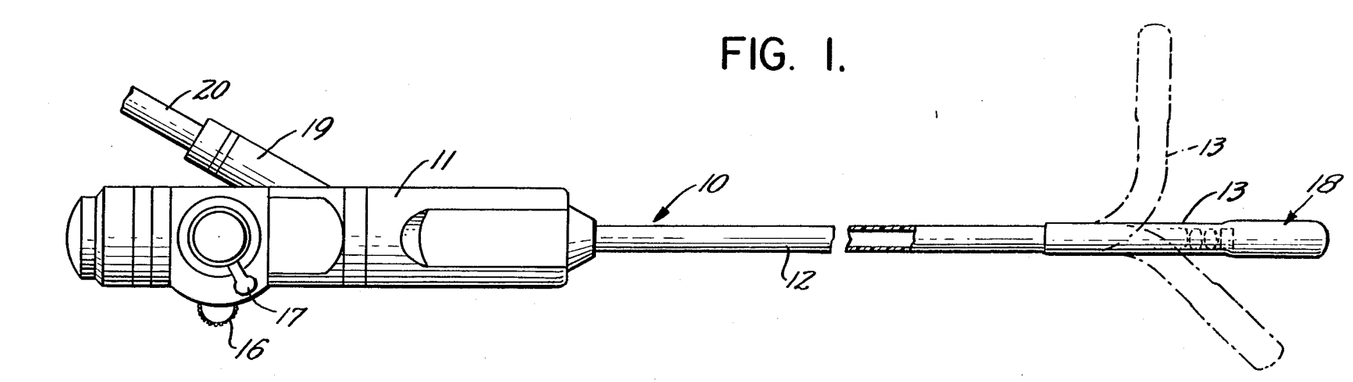
FIG. 1 is a plan view of an endoscope device having a controllably bendable distal end and carrying at its distal end extremity a mechanical sector scanning capsule according to the invention.
Figure 2:
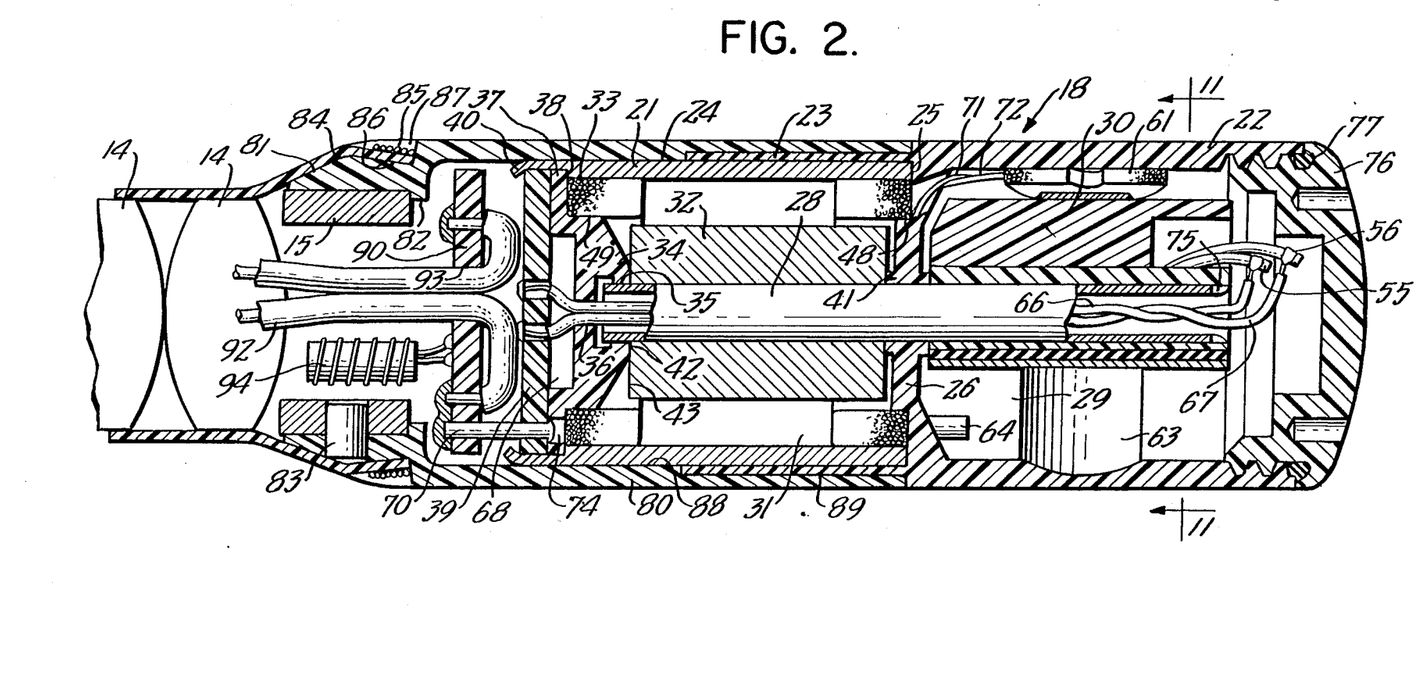
FIG. 2 is a highly enlarged, longitudinal cross sectional view of the transducer capsule of the invention, illustrating also the means for mounting the same at the end of an endoscope device.

Referring now to the drawing, and initially to FIGS. 1 and 2 thereof, the reference numeral 10 designates in a general way an endoscope device which for the most part, may be of a standard commercial type, such as MACHIDA GT-8-60US. The endoscope device includes a control handle 11, and a guide tube 12 provided with a manipulatable distal end 13. The endoscope device, which per se forms no part of the invention, is formed at its distal end by a plurality of hingedly connected link members 14 and a terminal collar member 15. A pair of control wires (not shown) extend through the guide tube 12 and are connected at their distal ends to the hinged links 14. At the remote end of the device, the control handle 11 is provided with a movable manipulating lever 16 which can be pivoted in one direction or the other to deflect the distal end of the endoscope, as indicated in phantom lines in FIG. 1. Typically, a locking lever 17 is provided to secure the endoscope in an adjusted position.

In the illustrated device, a transducer capsule 18 is secured to the end extremity of the endoscope. Conductor wires, for operating the transducer capsule and deriving its output are passed through the guide tube 12 and exit the device through an outlet tube 19 and cable 20. The cable 20 leads to an electronic control station, including operating controls, CRT etc. (not shown), all of which may be entirely conventional insofar as this invention is concerned.

With reference now to FIG. 2, the transducer capsule 18 comprises two primary housing parts 21, 22. The first housing part 21 is of thin wall, tubular construction and is formed of magnetic material, such as soft steel. Representative dimensions of the magnetic housing part 21 for the illustrated device are approximately 0.354 inch in outside diameter, wall thickness of approximately 0.020 inch and length of approximately 0.425 inch. The second principal housing part 22 is formed of a plastic material substantially transparent to ultrasonic acoustic pulses, and desirably having an acoustic impedance similar to that of the human body. A preferable material for this purpose is TPX a poly (4-methyl-pentene-1) molding resin marketed by Matsui and ICI. High density polyethylene and polypropylene are also acceptable materials.

Typical (i.e. nonlimiting) dimensions for the second housing part 22 are 0.406 inch principal outside diameter and principal wall thickness of about 0.030 inch. Advantageously, the outer housing part 22 is provided with a cylindrical wall extension 23 arranged to be telescopically received around the outer surface 24 of the metallic sleeve 21. In the assembled device, the mic tubing. A pair of conductor wires 66, 67 extend coaxially through the tubular shaft 28 and are attached at their outer ends to the crystal conductors 55, 56. At their inner ends, the conductors 66, 67 are connected to the terminal plate 39. To accommodate this, the back of the bearing member 34 is recessed at 68, to allow the conductors 66, 67 to be redirected after passing through the opening 36.

Figure 11:
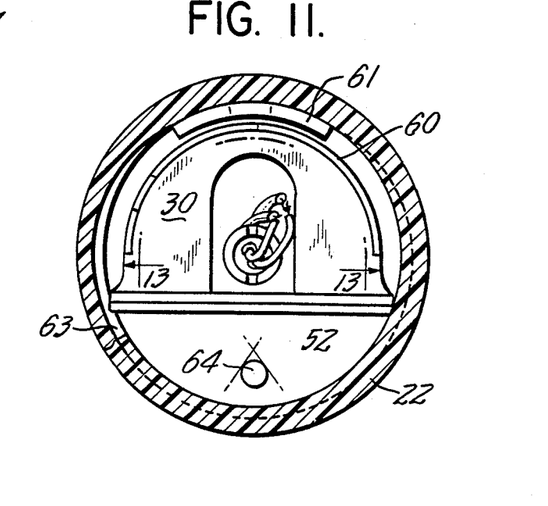
FIG. 11 is a cross sectional view as taken generally on line 11—11 of FIG. 2, illustrating the manner of mounting the transducer device within the capsule housing.
Figure 12:
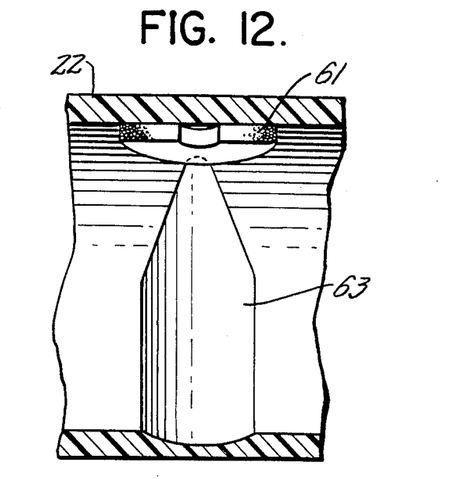
FIG. 12 is a fragmentary, longitudinal cross sectional view through one of the housing sections.

As will be appreciated, the maximum angular displacement of the transducer device 30 may be on the order of about 60° to either side from the "neutral" position, as shown in FIG. 11. During normal operations, the angular displacement typically would be somewhat less. This amount of angular displacement is easily accommodated in a fatigue-free manner by a slight twisting of the conductors 66, 67 over their relatively substantial longitudinal extent as they pass through the center of the tubular shaft 28.

Figure 3:
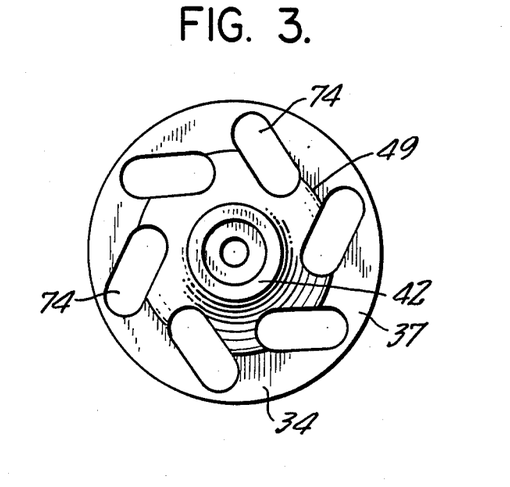
FIG. 3 is an axial end view of one of the shaft bearing members utilized in the new transducer unit.

In the device of the invention, external electrical connections are provided by a plurality of axially disposed terminal pins 70, which are fixed in the terminal plate 39. The terminal plate 39 is constructed in the form of a printed circuit board having connections for (in the illustrated version of the device) six conductors: The two conductors 66, 67 for energizing the transducer and for transmitting its echo signals; two pairs of conductors (not shown) for the motor coils 33, and a pair of conductors 71, 72 leading to the sensing coil 61. The sensing coil conductors extend through one of the openings 73 in the partition wall 26, along the V-shaped notch 47 between adjacent motor coils, to soldered terminals on the terminal plate 39. Printed circuit connections (not shown) connect each of the conductors with a corresponding terminal pin 70, of which six such pins would be provided in the illustrated device. The confronting face of the bearing member 34 is provided with a series of recesses 74 (see FIG. 3) to accommodate the circuit paths and soldering connections on the terminal plate 39.

In the assembly of the transducer capsule 18, the sleeve-like housing parts 21, 22 are telescopically assembled and secured by adhesive. The sense coil 61 is installed and secured by adhesive, as are the motor energizing coils 33. The tubular shaft 28, with the rotor mounted thereon are inserted into the bearing of the partition wall 26, after which the bearing 34 may be put in position and secured by adhesive. After installing the various wires on the terminal board 39, the board is placed in position, sealed with adhesive and mechanically secured by crimping of the sleeve end 40. The transducer device can now be installed on the shaft and secured by adhesive. A slot 75 in the end of the tubular shaft allows the shaft to be held while the transducer device is properly oriented relative to the magnetic orientation of the rotor 32 and the orientation of the coils 33, so that the transducer device is in its middle or neutral position relative to the sensing coil, as shown in FIG. 11, when the rotor 32 is in its neutral position relative to the energizing coils 33. The conductors 66, 67 may then be attached to the transducer conductors 55, 56, following which the capsule is filled with an appropriate acoustic coupling fluid, such as olive oil or castor oil. All traces of air must, of course, be positively excluded. After filling with oil, the capsule is sealed by applying a threaded cap 76, which may also be provided with an O-ring 77.

The transducer capsule thus described is entirely self-contained and ready for operation. All of the necessary input and output connections are available the terminal pins 70.

For mounting of the transducer capsule 18 to the end of the guide tube 12, there is provided a transition member 80, in the form of a generally cylindrical sleeve formed of a suitable plastic material, such as TPX. The transition member is provided at its inner end with a neck portion 81 which is telescopically received over the terminal collar 15 of the guide tube. The neck portion is applied over the collar until seated against a flange 82, after which it is secured by a pin 83 and typically also by adhesive. To accommodate this assembly procedure, the outer sleeve 84 of the guide tube is initially retracted or rolled back to expose the collar 15. Thereafter, the sleeve is returned to the position shown in FIG. 2 and secured by adhesive and by tightly wound threads 85. To enhance the securement of the sleeve 84, the neck 81 desirably has a surface 86 tapering convergently toward the outer end of the sleeve 80. This also provides a recess for the reception of the threads 85. This recess is then filled and smoothed with a suitable plastic material 87.

In the illustrated device, the transition member 80 has a stepped internal surface, including a first portion 88, which is received closely about the outer surface of the metallic sleeve 21, and a second portion 89, which is closely received over the cylindrical extension 23 of the outer housing part 22. Suitable adhesives are utilized to secure these several parts to each other Although the transducer capsule 18 is formed in part by the metallic sleeve 21, which forms a flux return path for the motor coils, it is very undesirable to have any metal exposed on the exterior of the device, which could come in contact with the patient. Accordingly, the transition 80 and outer housing part 22, between them, completely enclose the metal sleeve 21 with a plastic covering. By providing for an overlapping arrangement of all three elements, a superior structural arrangement is provided.

Prior to insertion of the capsule 18 into the transition member 80, the electrical connections are completed. A first step in this process is the connection of a socket plate 90 to various conductors extending down through the guide tube 12. In the illustrated arrangement, six conductors may be employed, two of which are reflected at 91 in FIG. 2. These are passed through a central opening 93 in the socket plate and directed to appropriate terminal points, to which they are soldered. The socket plate 90, in this respect, is in the form of a printed circuit board having desired connection points and conductor paths. In addition to the conductor connection points, the socket plate 90 is provided with openings for the reception of terminal pins 70 from the transducer capsule. The socket plate may also mount a small tuning inductor 94, which is connected in parallel with the transducer conductors 55, 56.

To establish the electrical connections during manufacture, the conductors extending through the guide tube are pushed axially downward through the guide tube, far enough to project out beyond the transition member 80. This allows the various conductors to be properly attached and soldered to the socket plate 90. Thereafter, the transducer capsule may be simply "plugged in" to the socket board, and the terminal pins 70 advantageously are soldered thereto for good electrical contact. When the transducer capsule is inserted into the transition member 80, the conductors may be simultaneously retracted into the guide tube as needed.

metallic sleeve seated against an abutment surface 25 formed at the inner end of the plastic housing section 22. In the finished device, the extension 23 is adhesively bonded to the metallic housing section 21, forming a sealed, rigid joint.

The plastic housing part 22 is provided with an integral partition wall 26 provided with a central bore 27 forming a forward journal bearing for a shaft 28. The partition wall 26 forms the inner end of a chamber 29 housing an ultrasonic transducer device 30. The partition 26 also forms the outer end of a chamber 31 housing a magnetic rotor 32 and coils 33 of a drive motor.

At the inner end of the rotor chamber 31 there is mounted a bearing member 34, formed of an engineering plastic, such as Delrin. The bearing 34 has a blind bore 35, which forms an inboard bearing for the shaft 28. This is connected to a smaller bore 36 for the passage of conductor wires, as will be further described. The bearing member 34 has a flange 37, which is seated against a shoulder 38 on the metallic housing part 21 for precise positioning of the bearing member.

A sealed inner end closure for the capsule 18 is formed by means of a terminal plate 39, to be further described, which is seated against the inner face of the bearing 34 and is secured mechanically by bending over of sleeve extensions 40 of the metallic housing part 21. A suitable bonding adhesive is applied prior to the crimping of the sleeve portions 40, to assure a fluid-tight closure.

In accordance with the invention, the magnetic rotor element 32 is fixed to a shaft 28, as by a suitable adhesive. Desirably, the rotor member 32 is formed of a so-called rare earth material of very high magnetizing force, i.e., at least about $20 \times 10^6$ gauss-oersteds. Desirable for this purpose are neodymium-iron-boron type alloys. The rotor element 32 has typical dimensions of about 0.200 diameter, 0.295 length. The magnetic material is polarized north and south on opposite diametral sides.

To advantage, the partition wall 26 and bearing member 34 are provided with inwardly facing axial bearing surfaces 41, 42 arranged in substantially contacting relation to end surfaces 43 of the rotor member 32. Accordingly, in the assembled unit, the rotor 32, shaft 28 and transducer unit 30 are all fixed axially by means of the axial bearings 41, 42.

Figure 4:
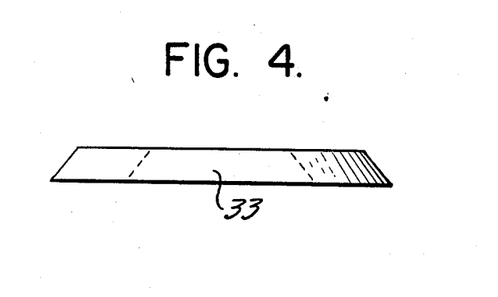
FIGS. 4 and 5 are elevational and plan views respectively of a motor coil used in the device of the invention, shown in flat form as originally wound.
Figure 5:
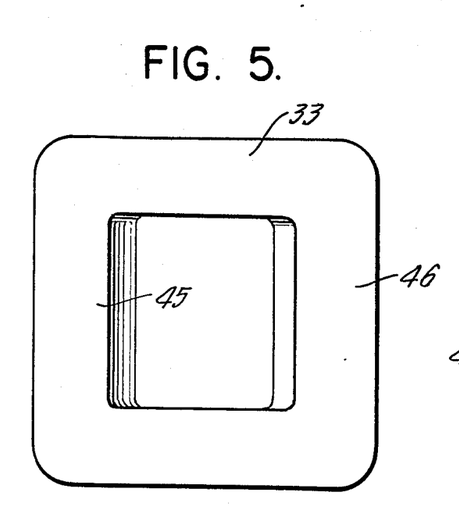
Figure 6:
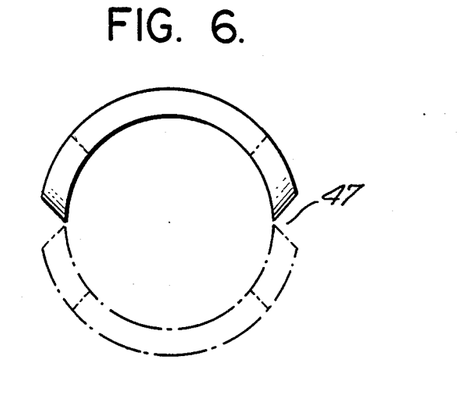
FIGS. 6 and 7 are end elevational and perspective views illustrating a pair of motor coils shaped into semi-cylindrical configuration for use in the device of FIG. 2.
Figure 7:
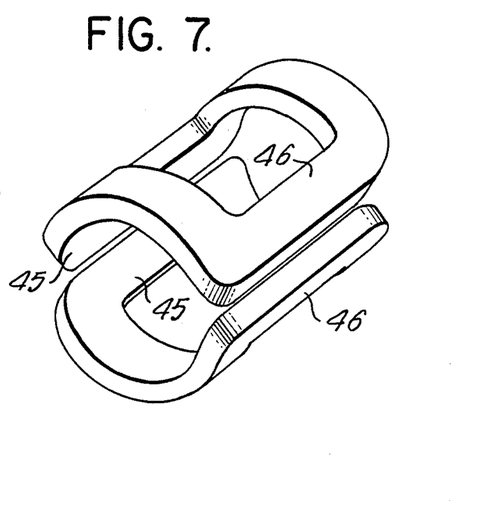

Energizing coils 33 for the drive motor advantageously are of a generally rectangular developed configuration, as shown in FIG. 5. For optimum efficiency, axially extending portions 45, 46 of the coils are as long as practicable, in relation to the length of the rotor 32 and thus the coils somewhat overhang the ends of the rotor. To simplify manufacture, the coils 33 may be wound in flat form, as reflected in FIG. 4. After winding, the coils are shaped around a cylindrical form, taking on a saddle-shaped, semi-cylindrical configuration, as reflected in FIGS. 6 and 7. The overall width of the coils is such that the respective axial coil portions 45—45 and 46—46 are in relatively closely spaced relation, in the assembled motor, leaving a small V-shaped gap 47 (see FIG. 6). In the illustrated structure, the partition wall 26 and the bearing wall 34 are provided with annular surfaces 48, 49 which underlie and support the energizing coils 33.

Figure 8:
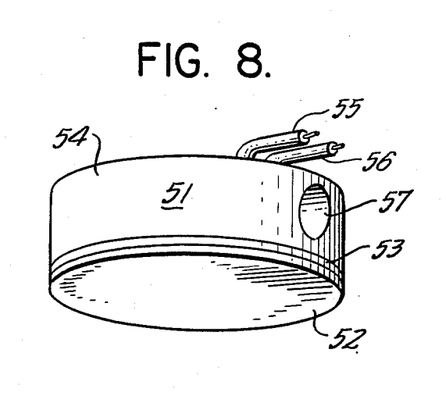
FIG. 8 is a perspective view of a transducer element utilized in the device of FIG. 2.
Figure 9:
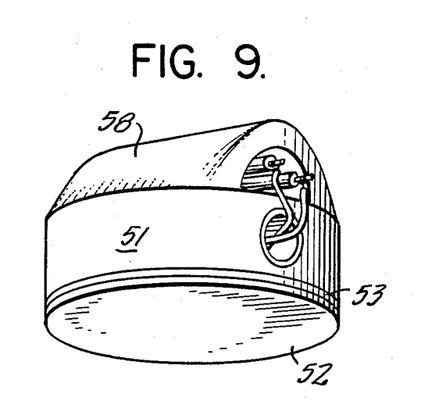
FIG. 9 is a perspective view, similar to FIG. 8, showing the transducer element attached to a generally semi-cylindrical body member.
Figure 10:
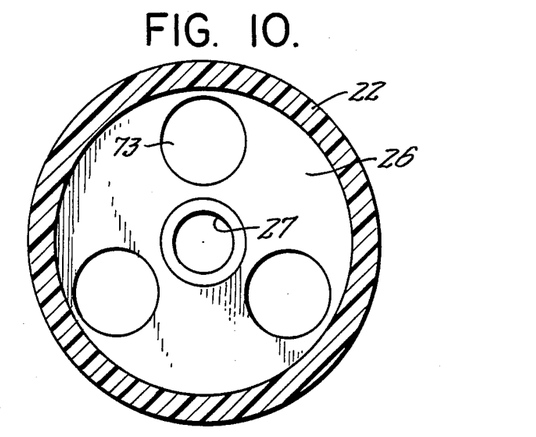
FIG. 10 is a cross sectional view through a section of the capsule housing, illustrating another of the shaft bearing portions.

Mounted on the forward extension 50 of the shaft 28 is the transducer device 30, certain details of which are illustrated in FIGS. 8, 9 and 11, as well as in FIG. 2. The principal transducer element 51 (see FIG. 8) comprises a thin, disc-like piezoelectric crystal 52, advantageously of circular configuration. The crystal 52 is mounted on a thin attenuating layer 53, which is in turn mounted on a plastic base 54. Conductors 55, 56 are appropriately connected to the crystal wafer 52 and, upon appropriate energizing of the conductors, the crystal 52 will emit acoustic pulses in a well known manner. Electrical signals are also generated by the crystal when it is stimulated acoustically. The plastic-base 54 is provided with a central axial bore 57, which is received on the shaft 28 and bonded thereto with a suitable adhesive.

In the illustrated form of the invention, the transducer device 30 includes a semi-cylindrical body member 58, which is mounted upon the crystal base 54. The body member 58 serves two purposes in the illustrated device. One purpose is to make the crystal device somewhat more hydrodynamic in its shape, to facilitate relatively rapid oscillating motion of the crystal within a body of oil contained in the capsule housing. As a second function, the body member 58 provides an appropriate outer surface, coaxial with the shaft 28, for the mounting of a shaped foil member 60 (see FIG. 13) arranged to cooperate with a sensing coil 61 for locating and controlling the angular position of the transducer device 30 relative to its housing. In any operative rotary position of the transducer device, a different width portion of the foil sensing element 60 will be located opposite the sensing coil 61. This changes the electrical characteristics of the coil, and this is fed through conductors back to a main control console (not shown but may be of conventional type). By this means, the instantaneous angular orientation of the transducer device relative to the housing can be determined at all times. Additionally, insofar as the momentary angular position of the device may vary with respect to a desired, preprogrammed orientation, the energizing of the driving motor can be varied for instantaneous correction. The circuitry for a control of this type is disclosed in, for example, the Matzuk U.S. Pat. No. 4,092,867.

To particular advantage, the design of the transducer device 30 of the present invention, is such as to allow the crystal wafer 52 to be located as closely as practicable to the center axis of the capsule 18. This enables the diameter of the crystal to be maximized in relation to the external dimensions of the capsule. Further, in this regard, the internal wall of the housing part 22 may be milled out slightly to form an annular groove in its lower portions, as reflected at 63, allowing the diameter of the crystal to be even slightly larger than would otherwise be permitted by the sleeve-like housing part 22 (see FIG. 11), for example. Desirably, the milled arcuate groove 63 terminates in the upper portion of the housing part 22, so that the strength of the housing is maintained, and the sense coil 61 is provided with a smooth, flat area for adhesive securement to the housing.

In normal operation of the device, the transducer device 30 is driven by the rotor 32 to oscillate through an angle which is both varied and controlled electronically at the control station. A stop pin 64 is nevertheless provided, extending from the partition wall 26, to physically limit the maximum angular displacement of the transducer device, shaft and rotor. This is desirable so that the parts do not assume an undesirable orientation during periods of nonuse.

Figure 14:
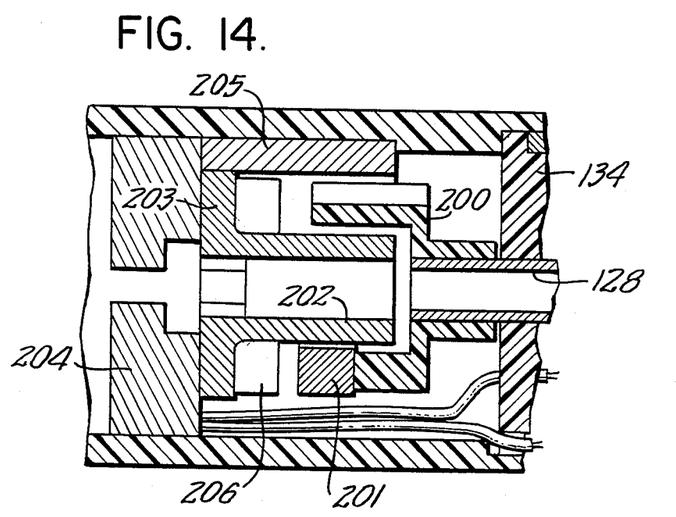
FIG. 14 is a fragmentary, longitudinal cross sectional view, illustrating a modified form of device for sensing the angular position of the transducer element.

In accordance with one feature of the invention, the shaft 28 is of tubular construction, desirably of a material such as T316 stainless steel, 16RW gauge hypoder- In the embodiment of the invention shown in FIG. 14, a modified form of position-sensing means is provided. In place of the sensing coil 61 and metal foil 60, of the previously described embodiment, a variable inductor arrangement is provided. The variable inductor device may be mounted at either end of the tubular shaft 128. In the illustration of FIG. 14, it is mounted at the rearward end closest to the guide tube of the endoscope. In the FIG. 14 version, the shaft 128 extends rearward somewhat beyond the bearing member 134 and has mounted thereon a plastic hub 200 which carries a magnetic element 201 in the form of an arc of a circle concentric about the axis of the shaft 128.

Opposite the shaft 128 is a sleeve 202, secured by a flange 203 to a partition wall 204. The sleeve and flange are of magnetic material and are partially surrounded by an external sleeve 205, also of magnetic material. The sleeve 205 is in the form of an incomplete cylinder. Typically, the arc of the magnetic element 201, together with the arc of the sleeve 205 total approximately slightly more than 360°.

A sensing coil 206 is wound about the internal sleeve 202, and the inductance of the coil is a variable function of the magnetic path provided by the sleeves 202, 205 and the movable magnetic element 201. In the "neutral" position of the shaft 128 (half way between the extremes of rotary displacement in either direction), the movable magnetic member 201 is symmetrically located relative to the gap in the incomplete sleeve 205. As the shaft is rotated in either direction, the movable magnetic element 201 becomes present to an increasingly greater extent between the walls of the respective sleeves 202, 205, causing progressive variation in the inductance of the coil 206, which can be utilized both as a means of locating the rotary position of the transducer and of correcting its position relative to a programmed cycle of motion.

Figures 13, 15:
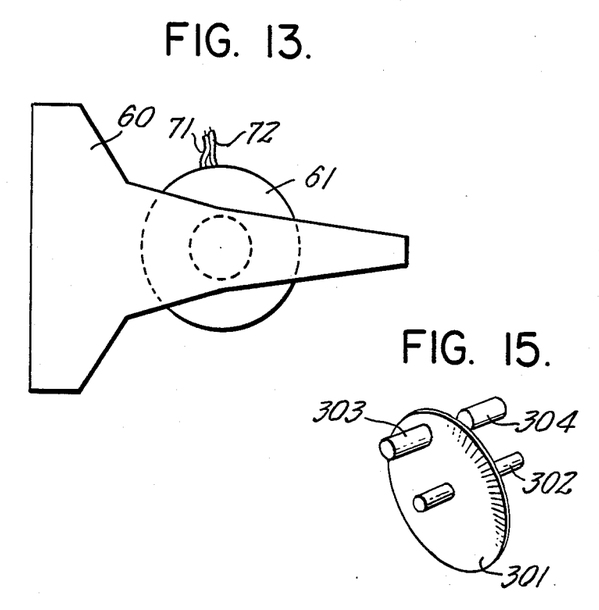
FIG. 13 is a simplified, developed representation of one form of position-sensing device utilized for sensing the angular position of the transducer element.
FIG. 15 is a simplified, schematic representation of another alternative form of position-sensing device, using optical means.

Other types of position-sensing devices may be utilized in the device of the invention, where desired. For example optical devices in themselves known in the art, may be attached to or driven by the shaft to provide an output of data. A representation of such device is shown in FIG. 15 and includes a calibrated transparent encoder disc 301 mounted on a shaft 328. Optical sensing means including light emitting and sensing devices 303, 304 detect the passage of the code marks for determining the exact position of the shaft (and transducer device driven thereby) at all times.

The device of the invention represents a significant advance in the design of mechanical sector scanning transducers, in that it enables a full function, rugged, reliable, precision device to be housed within a relatively minute capsule having a diameter of about ten mm and a total length of less than thirty mm. Within these limited dimensions, the device accommodates a transducer having a diameter of approximately 7.5 mm, providing for a high degree of power and image resolution in relation to the minimum size of the transducer capsule. For pediatric applications, the transducer capsule may be even smaller, for example, six mm diam. The smaller unit typically would be operated at a somewhat higher frequency (e.g, 7.5 MH as compared to 5 MH for an adult unit.)

By providing for a fixed structural relationship between the drive rotor, the shaft and the transducer, a high degree of precision is possible in the positioning of the transducer device and in the sensing of the transducer position, further adding to clarity, precision and resolution of the B-mode display of the scan.

A particularly advantageous feature of the device of the invention is its extremely low part count. Mounting of the rotor 32 and transducer device 30 in fixed relation on a common shaft provides for a high degree of simplification, which also translates into reduced cost and greater reliability. Further significant advantages in this connection are realized by the use of a hollow drive shaft and the passing of flexible conductors through the shaft for connection to the movable transducer device. This arrangement results in minimum stress and fatigue on the conductors, and basically occupies no otherwise useable space in the transducer capsule. Additionally, by locating the conductors on the center axis of the shaft, there is absolute minimum hydrodynamic resistance introduced thereby.

The construction of the capsule housing being formed in part by the metal sleeve 21, which surrounds the rotor and forms a return flux path, and in part by the acoustically transparent outer housing 22 further minimizes the complexity and part count by allowing an active element of the drive motor to form an active part of the capsule housing.

In the device of the invention, the transducer device is designed and mounted so that the active piezoelectric disc is located as close as practicable to the axis of the main drive shaft, which is as close as practicable to the maximum diameter of the transducer housing portion (e.g., see FIG. 11). And by forming an annular groove in the housing in this area, the diameter of the piezoelectric crystal may be even further slightly increased for maximum effectiveness.

The device of the invention represents a significant advance in the practice of transesophageal echocardiography, in that it provides a clinically practical mechanically operated sector scanner, which may be manufactured and marketed at a fraction of the cost of conventional array devices. Thus, whereas array scanning devices are operationally satisfactory, the cost thereof is so prohibitively high as to preclude use of the equipment in many cases where it would be desired. Mechanical sector scanners, although much less complex and less expensive to produce, have heretofore been altogether unsatisfactory, from a performance standpoint or from the standpoint of excessive size, or in many cases both.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

We claim:

1. An ultrasonic sector scanner for mounting at the distal end of an endoscope guide tube or the like and adapted for insertion into and operation within body cavities, which comprises
   (a) a housing including an elongated tubular housing section and spaced end walls forming a sealed enclosure,
   (b) a tubular shaft mounted within and substantially coaxially of said housing and supported therein for limited rotation through an angle of less than 360°.
   (c) a generally cylindrical magnetic rotor mounted coaxially on an inner end portion of said shaft and rotatable therewith, (d) a portion of said tubular housing section surrounding said magnetic rotor being formed of magnetic material, (e) an ultrasonic transducer unit fixed to an outer end portion of said shaft spaced axially from said rotor and rotatable therewith, (f) said ultrasonic transducer unit further including a body member and comprising a disc-like transducer crystal element mounted on said body member and disposed with its axis generally perpendicular to the axis of said shaft and being mounted closely adjacent to the axis of said shaft, and (g) flexible conductor means extending through said tubular shaft and connected at one end to said transducer unit for activating the same, (h) one of said housing end walls having terminal conductors passing therethrough in sealed relation, (i) said flexible conductor means being connected at their other ends to said terminal conductors.

2. An ultrasonic sector scanner according to claim 1, further characterized by
(a) said body member having cylindrically contoured surface portions generally concentric with the axis of said shaft,
(b) a shaped foil extending circumferentially about the cylindrically contoured surface portions of said body member,
(c) a position sensing coil mounted on the inside of said housing, in alignment with said foil and operative to provide an electrical signal corresponding to the angular position of said shaft and body member.

3. An ultrasonic sector scanner according to claim 1, further characterized by
(a) said housing comprising a first tubular section formed of plastic material, substantially transparent to ultrasonic acoustical energy, surrounding said transducer unit,
(b) said housing further comprising a second tubular section formed of magnetic material, surrounding said magnetic rotor and joined coaxially with said first tubular section,
(c) said second tubular section forming part of a magnetic circuit cooperating with said magnetic rotor.

4. An ultrasonic sector scanner according to claim 3, further characterized by
(a) said first tubular housing section having a transverse wall positioned between said transducer unit and said magnetic rotor and forming a first bearing for said tubular shaft,
(b) a second bearing mounted at the end of said second tubular section and supporting one end of said tubular shaft,
(c) said first and second bearings having end surfaces cooperating with said magnetic rotor to form axial thrust bearings for fixing the axial position of said rotor member, shaft and transducer unit.

5. An ultrasonic sector scanner according to claim 4, further characterized by
(a) electrical motor coils of arcuate cross sectional configuration mounted within said second tubular housing section and closely embracing said magnetic rotor,
(b) said motor coils being controllably energizable for driving said rotor in either direction through a limited sector angle,
(c) said transverse wall and said second bearing having annular support surfaces thereon of slightly larger diameter than the diameter of said rotor, for supporting said motor coils in closely spaced relation to said rotor.

6. An ultrasonic sector scanner according to claim 5, further characterized by
(a) the end wall of said second tubular section is formed by a conductor terminal plate mounted in sealed relation with said second tubular housing section,
(b) terminal conductor means passing through said terminal plate in sealed relation,
(c) said terminal conductor means being connected to conductors internally and externally of said sealed housing for driving and controlling the sector scanner and deriving its output.

7. An ultrasonic sector scanner according to claim 6, further characterized by
(a) said terminal plate having a plurality of terminal pins mounted thereon and projecting axially outward from said plate,
(b) circuit means providing conductive connection from selected terminal pins to selected conductors within said housing, and
(c) a socket plate, separate from said sector scanner unit, adapted for conductive reception of said terminal pins for connection of said scanner unit with external means.

8. An ultrasonic sector scanner according to claim 3, further including
(a) a tubular transition member formed of plastic material and adapted for mounting at one end to the distal end of an endoscope guide tube,
(b) one or both of said transition member and said first tubular housing section telescopically overlapping said second tubular housing section externally over its length.

9. An ultrasonic sector scanner according to claim 8, further characterized by
(a) said first tubular housing section partially externally overlapping said second tubular housing section and being secured thereto, and
(b) said tubular transition member partially externally overlapping said second tubular housing section and said first tubular housing section and being secured thereto.

10. An endoscope adapted for transesophageal echocardiography, which comprises
(a) an elongated guide tube having a controllably bendable distal end and control means therefor at its proximal end,
(b) a sector scanning ultrasonic transducer capsule mounted at the distal end of said guide tube,
(c) said transducer capsule comprising a cylindrical housing structure including a first cylindrical sleeve of magnetic material and a second cylindrical sleeve of acoustically transparent material joined to said first sleeve in coaxial relation,
(d) outer end walls forming with said sleeves a sealed cylindrical capsule housing,
(e) a shaft disposed coaxially within said sealed housing and journalled for limited rotation therein,
(f) a magnetic rotor fixed on said shaft for rotation within said first cylindrical sleeve,
(g) an ultrasonic transducer element fixed to said shaft for rotation within said second cylindrical sleeve, (h) said transducer element being mounted closely adjacent to said shaft and oriented with its axis perpendicular to the axis of said shaft.

(i) said sealed housing being fixed to the distal end of said guide tube in coaxial relation.

11. An endoscope according to claim 10, further characterized by
(a) said first cylindrical sleeve forming a wall portion for said sealed housing, and
(b) said outer end walls being secured to said first and second sleeves respectively.

12. An endoscope according to claim 10, further characterized by
(a) a transition sleeve formed of plastic material fixed to the distal end of said guide tube and mounting said sealed housing,
(b) at least one of said second cylindrical sleeve or said transition sleeve being in externally telescoping relation with said first cylindrical sleeve,
(c) said sealed housing and said transition sleeve being coaxially aligned with the distal end of said guide tube.

13. An endoscope according to claim 10, further characterized by
(a) the end wall of said sealed housing adjacent said guide tube being formed by a terminal plate having a plurality of axially extending terminal pins,
(b) a plurality of electrical conductors extending through said guide tube for connection with said sealed housing,
(c) a socket plate electrically connected with said conductors adjacent the distal end of said guide tube,
(d) said the pins of said terminal plate being received in said socket plate for connection of said conductors within the interior of said sealed housing.

14. An ultrasonic transducer capsule adapted particularly for use in transesophageal echocardiography, which comprises
(a) an elongated, sealed tubular housing adapted for coaxial mounting at the end of an endoscope guide tube,
(b) a first axial portion of said sealed housing including a sleeve of magnetic material,
(c) a second axial portion of said housing being formed of acoustically transparent material,
(d) a shaft mounted coaxially within said sealed housing for rotation through a limited sector scanning arc,
(e) a magnetic rotor element fixed to said shaft for rotation therewith within said first axial housing portion,
(f) electrically energizable coil means within said first axial housing portion for bi-directional rotation of said rotor element,
(g) an ultrasonic transducer element fixed to said shaft for rotation therewith within said second axial housing portion,
(h) said transducer element being mounted closely adjacent to said shaft and oriented with its axis perpendicular to the axis of said shaft.
(i) stop means within said sealed housing for limiting rotation of said shaft, motor element and transducer to an angle of less than 360°.

15. An ultrasonic transducer capsule according to claim 14, further characterized by
(a) said second axial housing portion having an end portion partially telescopically received over the exterior surface of said first axial housing portion,
(b) a transition sleeve formed of plastic material having an end portion partially telescopically received over the exterior surface of said first axial housing portion and, together with said second axial housing portion forming a cylindrical outer surface completely surrounding said first axial housing portion, and
(c) means on said transition sleeve for mounting said sleeve and said transducer unit coaxially at the end of an endoscope guide tube.

16. An ultrasonic transducer capsule according to claim 14, further characterized by
(a) said shaft being of tubular construction,
(b) conductor wires extending axially through said tubular shaft,
(c) said conductor wires being fixed at one end to one end of said sealed housing and being fixed at the other end to said transducer element and movable therewith during sector scanning oscillations of said transducer element.

17. An ultrasonic transducer capsule according to claim 14, further characterized by
(a) first and second shaft bearings positioned within said sealed housing and journalling said shaft,
(b) said shaft bearings having axial bearing surfaces cooperating with opposite ends of said rotor element to axially confine said rotor element and thereby position axially said shaft and transducer.

18. An ultrasonic transducer capsule according to claim 14, further characterized by
(a) position sensing means for determining the rotary position of said transducer element within said housing,
(b) said position sensing means comprising a sensing coil carried on an inner wall of said second axial housing portion and a shaped foil carried on said transducer element and movable with respect to said sensing coil upon rotation of said shaft.

19. An ultrasonic transducer capsule according to claim 14, further characterized by
(a) position sensing means for determining the rotary position of said transducer element within said housing,
(b) said position sensing means comprising a first arcuate member, formed of magnetic material and mounted in said housing in fixed relation thereto,
(c) said position sensing means further comprising a second arcuate member, formed of magnetic material and mounted on said shaft for rotation therewith.

20. An ultrasonic transducer capsule according to claim 14, further characterized by
(a) position sensing means for determining the rotary position of said transducer element within said housing,
(b) said position sensing means comprising optical sensing means.

21. An ultrasonic transducer capsule according to claim 20, further characterized by
(a) said optical sensing means comprising light emitting and sensing elements, and a member mounted on said shaft and positioned between said light emitting and sensing elements for affecting the passage of light as a function of the position of said shaft.

22. In an ultrasonic endoscope apparatus of the type including an elongated guide tube assembly having a controllably bendable distal end and an ultrasonic sector scanner mounted at said distal end, an improved sector scanner comprising
  (a) an elongated sealed tubular housing,
  (b) a partition in said housing forming a shaft bearing,
  (c) a tubular shaft journalled in said bearing and extending axially within said housing,
  (d) a magnetic rotor fixed to one portion of said shaft of one axial side of said bearing,
  (e) an ultrasonic transducer fixed to said shaft on the other axial side of said bearing closely adjacent the axis of said shaft and oriented at right angles thereto,
  (f) end wall forming means at opposite ends of said tubular housing forming therewith a sealed enclosure for the containment of liquid,
  (g) at least a portion of said housing surrounding said rotor being formed of magnetic material,
  (h) at least a portion of said housing surrounding said transducer being formed of material substantially transparent to ultrasonic energy,
  (i) one of said end walls having electrical terminal conductors passing therethrough in sealed relation,
  (j) transducer activating electrical conductor means connected to said transducer, extending axially through said tubular shaft and connected to certain of said terminal conductors,
  (k) rotor driving coils mounted within said magnetic material housing portion,
  (1) coil energizing conductors connected respectively to said coils and to certain ones of said terminal conductors,
  (m) position sensing means within said sealed enclosure for determining the angular position of said transducer, and
  (n) control means including said position sensing means for controllably oscillating said rotor, shaft and transducer through a limited sector scanning angle.

23. An ultrasonic endoscope apparatus according to claim 22, further characterized by
  (a) the portion of said tubular shaft mounting said transducer being unsupported at the end thereof remote from said partition, and
  (b) bearing means in said housing for supporting said shaft adjacent the end of the portion thereof mounting said rotor.

* * * * *